United States Patent [19]

Narula

[11] Patent Number: 4,788,001
[45] Date of Patent: Nov. 29, 1988

[54] OIL-IN-WATER EMULSION

[75] Inventor: Dipak Narula, Midland, Mich.

[73] Assignee: Dow Corning Corporation, Midland, Mich.

[21] Appl. No.: 912,020

[22] Filed: Sep. 26, 1986

Related U.S. Application Data

[63] Continuation-in-part of Ser. No. 718,974, Apr. 2, 1985, abandoned.

[51] Int. Cl.$^4$ .................... B01J 13/00; C09K 3/00
[52] U.S. Cl. .................... 252/312; 106/287.13; 106/287.14; 252/315.4; 252/356; 252/DIG. 1; 424/65; 514/941; 514/944
[58] Field of Search .................... 252/312; 106/287.13, 106/287.14; 514/941

[56] References Cited

U.S. PATENT DOCUMENTS

| | | | |
|---|---|---|---|
| 2,702,276 | 2/1955 | Green | 252/8.6 |
| 2,755,194 | 7/1956 | Volkmann et al. | 106/285 |
| 2,891,920 | 6/1959 | Hyde et al. | 260/29.2 |
| 3,136,696 | 6/1964 | Harrison | 106/287.13 X |
| 3,294,725 | 12/1966 | Findlay et al. | 260/29.2 |
| 3,360,491 | 12/1967 | Axon | 260/29.2 |
| 3,641,181 | 2/1972 | Robbins et al. | 252/312 X |
| 3,795,538 | 3/1974 | Evans et al. | 117/139.5 |
| 4,177,177 | 12/1979 | Vanderhoff et al. | 260/29.2 |
| 4,194,988 | 3/1980 | Schneider et al. | 252/312 |
| 4,310,678 | 1/1982 | Blizzard et al. | 556/451 |
| 4,388,437 | 6/1983 | Ona | 106/287.13 X |
| 4,501,619 | 2/1985 | Gee | 106/287.13 X |
| 4,509,981 | 4/1985 | Sanders, Jr. et al. | 106/287.13 X |
| 4,518,727 | 5/1985 | Traver | 106/287.13 X |

FOREIGN PATENT DOCUMENTS 2072016 9/1981 United Kingdom .................... 514/941

OTHER PUBLICATIONS

Glucate SS Glucamate SSE-20-Nonionic Emulsifiers Multifunctional Glucose Derivatives, © 1978 Americhol Corporation.
Glucamate Doe-120-Nonionic Viscosity Enhancer, Americhol Corporation, May 1986.
McCutcheon's Detergents and Emulsifiers, North American Edition, 1975, pp. 22,24,26,28,29 and 30.

Primary Examiner—Richard D. Lovering
Attorney, Agent, or Firm—George A. Grindahl

[57] ABSTRACT

Oil-in-water emulsions are provided by a process which involves the mixing of the oil and water in the presence of three nonionic surfactants having certain HLB values. The process is particularly useful for emulsifying an oil having a viscosity exceeding 50,000 centipoise (50 pascal-seconds). Any oil can be emulsified by this process, including hydrocarbon oils like mineral oil and petrolatum, and silicones, including fluids, gums and resins. A particularly useful emulsion prepared by this process is an emulsion of a bi-modal silicone which contains substantial amounts of a volatile silicone and a silicone gum.

23 Claims, No Drawings

OIL-IN-WATER EMULSION

BACKGROUND OF THE INVENTION

This application is a continuation-in-part of U.S. Ser. No. 718,974; filed on Apr. 2, 1985.

The present invention relates generally to oil-in-water emulsions and to a process for their preparation using only nonionic surfactants. In particular the present invention relates to a process for emulsifying high-viscosity silicone fluids, gums and resins.

Aqueous emulsions of silicones, including high viscosity silicones, have been prepared by emulsion polymerization of a silicon-containing monomer (Hyde et al., U.S. Pat. No. 2,891,920; Findlay et al., U.S. Pat. No. 3,294,725; and Axon, U.S. Pat. No. 3,360,491) and by direct emulsification of a preformed silicone (Green, U.S. Pat. No. 2,702,276; Volkmann et al., U.S. Pat. No. 2,755,194 and Schneider et al., U.S. Pat. No. 4,194,988). However, these processes use one or more surfactants of the ionic type for the formation and/or stabilization of the emulsion and are therefore not suitable for use in the many applications which require the absence of anionic and cationic species in the emulsion.

Evans et al., U.S. Pat. No. 3,795,538 teach a process for emulsifying a polydiorganosiloxane fluid in water using only nonionic surfactants; however, the emulsification of silicone gums, bi-modal silicones and silicone resins are not contemplated or disclosed therein.

Vanderhoff et al., U.S. Pat. No. 4,177,177, teach a two-step process for emulsifying a polymer phase having a viscosity of less than about 10,000 centipoise (10 pascal-seconds) in an aqueous medium containing at least one oil-in-water functioning emulsifier, in the presence of an additive to increase the stability of the final emulsion. However, Patentees' process is not suitable for emulsifying a polymer phase having a viscosity of over 10,000 centipoise.

As disclosed in copending application U.S. Ser. No. 718,984, entitled "Substantive Skin Care Compositions Comprising a Polydimethylsiloxane", filed on Apr. 2, 1985 and assigned to the assignee of the present invention, the incorporation of a polydimethylsiloxane having a viscosity of at least 30,000 centipoise (30 pascal-seconds) into a skin care composition increases the skin-substantivity of a skin care component formulated therein. While such high viscosity silicones can be incorporated into a nonaqueous skin care composition with the aid of a solvent therefor, their incorporation into an aqueous skin care composition has been prevented by the lack of a suitable aqueous emulsion thereof.

Copending application U.S. Ser. No. 718,985, entitled "Bi-modal Silicone Emulsions, Silicone Emulsification Process and Emulsions Therefrom", filed on Apr. 2, 1985 and assigned to the assignee of this invention, discloses aqueous emulsions of a polydimethylsiloxane fluid having a viscosity of up to 50 pascal-seconds at 25° C. and comprising a high viscosity silicone. These emulsions are useful as a substantivity aid in a skin care composition as noted above.

However, there is a need for aqueous emulsions comprising high viscosity silicones wherein the viscosity of the silicone exceeds 50 pascal-seconds. In particular, there is a need for aqueous emulsions of a bi-modal silicone component having a viscosity as high as 2,000 pascal-seconds and comprising as much as 50 percent silicone gum and 50 percent volatile silicone. The present invention provides those emulsions.

Copending and coassigned application for U.S. Pat. No. filed on Oct. 30, 1987 and entitled "Water-Based, Silicone-Organic Polymer Compositions and Method Therefor", U.S. Ser. No. 115,493 discloses a method for modifying the physical properties of an aqueous organic polymer composition by incorporating therein an aqueous emulsion of a polysiloxane resin. The present invention provides those emulsions.

BRIEF SUMMARY OF THE INVENTION

It is an object of the present invention to provide a method for preparing an aqueous emulsion of a high viscosity oil. It is a particular object of the present invention to provide an aqueous emulsion of a bi-modal silicone fluid having a viscosity in excess of 50,000 centipoise (50 pascal-seconds) and comprising substantial amounts of a volatile polydimethylsiloxane and a high viscosity, nonvolatile polydimethylsiloxane gum. It is further an object of this invention to provide a stable oil-in-water emulsion comprising a high viscosity silicone, and a process therefor, that comprises only nonionic surfactants. It is also an object of this invention to provide a process for preparing an aqueous emulsion of a high viscosity oil phase which does not require the use of additional heat to lower the viscosity of the oil phase.

These objects, and others which will occur to one skilled in the emulsion art upon considering the following disclosure and appended claims, are obtained by the present invention which, generally stated, comprises thoroughly mixing an oil phase and an aqueous phase in the presence of limited amounts of a primary, a secondary and a tertiary nonionic surfactant. In a preferred embodiment the oil phase has a viscosity of greater than 50,000 centipoise and the aqueous phase, comprising only a small amount of water, is admixed into the oil phase.

While not limiting the present invention by way of any particular theory I believe that the oil-in-water emulsions of this invention are produced and stabilized by the solubilizing and thickening action of the tertiary surfactant, in combination with the primary and secondary surfactants, so that a stable balance of emulsion particle size and emulsion viscosity is obtained.

DETAILED DESCRIPTION OF THE INVENTION

The present invention relates to a process for preparing an oil-in-water emulsion, and to the emulsions obtained thereby, said process comprising mixing an aqueous phase consisting essentially of at least 10 parts by weight of water and an oil phase consisting essentially of 100 parts by weight of a water-insoluble oil until the oil-in-water emulsion has been formed, said aqueous phase and/or said oil phase further containing, in total, at least 3 millimols of a nonionic primary surfactant having an HLB number of from 13 to 15; from 1 to 5 millimols, for every millimol of said nonionic primary surfactant, of a nonionic secondary surfactant having an HLB number of from 7 to 9; and at least 0.05 millimol of a nonionic tertiary surfactant having an HLB number of at least 16.

The process of this invention can be used to emulsify any water-insoluble oil into water. By the term oil it is meant herein a liquid or semi-solid material such as a freely flowing oligomer or a slowly flowing gum, ranging in viscosity from a few centipoise (millipascalseconds) to a few kilopascal-seconds or a non-flowing gel, and having a natural or synthetic origin. It is only necessary that the oil be mixable with other emulsion components, such as surfactants and water, using typical emulsifying means.

Examples of suitable water-insoluble oils for the emulsifying method of this invention include, but are not limited to, natural liquids, such as animal, vegetable and mineral oils, such as glycerides of fatty acids, extracts of seeds and nuts and petroleum and petroleum-derived oils such as machine oil and refined mineral oil or petrolatum liquid; natural resins such as oleoresins and gum resins; and synthetic liquids and resins, such as siloxane and organic condensation or addition polymer fluids, gums, elastomers and resins.

The water-insoluble oil is preferably a hydrocarbon oil or a silicone oil or mixtures thereof; examples of which include, but are not limited to, mineral oil, petrolatum, dimethylsilicones and their mixtures.

A silicone, for the purposes of this invention, is a compound having at least two silicon atoms per molecule and the average formula $R_aSiO_{(4-a)/2}$ wherein R denotes a hydrocarbon or substituted hydrocarbon radical, the substituents of which include, for example, radicals containing one or more atoms selected from the group consisting of nitrogen, oxygen, sulfur and halogen atoms, such as fluorine or chlorine atoms, and amido, amino, carboxy, epoxy or mercapto radicals.

Examples of suitable hydrocarbon radicals include alkyl radicals, such as methyl, ethyl, isopropyl, isobutyl, hexyl, octyl, dodecyl and octadecyl; alkenyl radicals, such as vinyl, allyl and cyclohexenyl; and aryl radicals, such as phenyl, benzyl and tolyl.

Examples of suitable substituted hydrocarbon radicals include chloropropyl, 3,3,3-trifluoropropyl, mercaptopropyl, amine-substituted radicals such as beta-aminoethylamine-substituted alkyl radicals and their partially or fully acylated derivatives, epoxy-substituted alkyl radicals such as glycidoxypropyl and carboxyalkyl radicals such as S-carboxymethylmercaptoethyl and its ester derivatives.

Silicones can further comprise various amounts of silicon-bonded radicals such as hydroxy, alkoxy and hydrogen.

The value of a in the above formula for a silicone can range from about 1 to 3 which gives rise to compositions ranging from silicone resins to branched silicones to cyclic silicones to linear silicones.

A dimethylsilicone is a compound having the unit formula $Me_2SiO_{2/2}$ and consisting of two or more of said units arranged in a cyclic and/or substantially linear molecular structure. Cyclic polydimethylsiloxanes have the formula $(Me_2SiO)_x$ wherein x has a value of at least 3. Substantially linear polydimethylsiloxanes have the formula $X(Me_2SiO)_ySiMe_2X$ wherein y has a value of at least 1 and X denotes a terminal radical such as hydrocarbyl, preferably having 1 to 6 carbon atoms, such as methyl, ethyl, vinyl and phenyl, hydroxy or alkoxy. Preferably X is methyl or hydroxy.

Herein the term silicone and the term organopolysiloxane are regarded as being synonymous and are used interchangeably. Similarly, the term dimethylsilicone and the term polydimethylsiloxane are regarded as being synonymous and are used interchangeably.

The silicone can consist essentially of a volatile or a nonvolatile silicone. Alternatively, the silicone can comprise a nonvolatile silicone and the normal amount, typically from 9 to 13 percent by weight, of volatile silicones that are produced during the normal siloxane equilibration process for preparing silicones. In addition the silicone can consist essentially of a nonvolatile silicone and a larger-than-normal amount of volatile silicone, such as 15, 20, 25 and more percent by weight.

Herein the distinction between a volatile silicone and a nonvolatile silicone is based on the normal boiling point of the silicone. Silicones which have a normal boiling point of less than 250° C. are designated as volatile silicones. All other silicones are designated as nonvolatile silicones.

Examples of volatile silicones suitable for use in this invention include cyclic polydimethylsiloxanes having the formula $(Me_2SiO)_x$ wherein x denotes 3, 4, 5 and 6 and methylterminated linear polydimethylsiloxanes having the formula $Me(Me_2SiO)_ySiMe_3$ wherein y has a value of 1, 2, 3 and 4.

Examples of nonvolatile silicones for the purposes of this invention include, but are not limited to, those linear and branched silicones having a viscosity at 25° C. of at least 30,000 centipoise (30 pascal-seconds), such as 30,000, 60,000, 100,000, 1,000,000 centipoise and more, and resinous silicones. For nonvolatile silicones having a viscosity exceeding 10 million centipoise it is preferred to use the well-known units of plasticity number as delineated in ASTM D926-67. Thus, for silicone viscosities ranging from 10 million to 20 million to 40 million to 80 million centipoise, corresponding values of plasticity number for a substantially linear silicone will range from 130 to 146 to 165 to about 203, respectively. Correspondingly, the number average molecular weight for dimethylsilicones will range from about 55,000 to about 350,000 as the viscosity ranges from 30 pascal-seconds to 100 kilopascal-seconds. Of course, suitable nonvolatile dimethylsilicones can contain trace amounts of polymer chain branching which will alter this viscosity-molecular weight relationship.

A preferred silicone for the process of this invention and for the composition of this invention is a bi-modal silicone. By a bi-modal silicone it is meant herein a silicone that consists essentially of a substantial amount, such as for example, from 25 to 99 percent by weight of a volatile silicone portion and from 1 to 75 percent by weight of a nonvolatile silicone portion having a viscosity of at least 30 pascal-seconds at 25° C.

A bi-modal silicone is preferred for at least two reasons. First, the presence of a substantial amount of volatile, and hence low viscosity, silicone portion reduces the apparent viscosity of the nonvolatile silicone, thereby allowing the use of a nonvolatile silicone portion having a viscosity of 10,000,000 centipoise (10 kilopascal-seconds) and more. Second, a bi-modal silicone component has a bi-modal efficacy in personal care compositions, i.e., the well-known efficacy of volatile silicones plus the above-noted substantivity-enhancing efficacy of a high viscosity silicone for certain skin care components, as well as other desirable effects such as water-repellency and lubrication.

A highly preferred silicone for the process and compositions of this invention is a bi-modal dimethylsilicone consisting essentially of 50 to 90 parts by weight of a volatile dimethylsilicone selected from octamethylcyclotetrasiloxane, decamethylcyclopentasiloxane, and their mixtures, and 10 to 50 parts by weight of a nonvolatile dimethylsilicone gum having a viscosity of at least 10 million centipoise (10 kilopascal-seconds) at 25° C.

A bi-modal dimethylsilicone comprising as little as 10 percent by weight of a dimethylsilicone gum is a highly effective component for skin care formulations with respect to its substantivity-enhancing effect and its esthetic effects. However, bi-modal silicones having higher dimethylsilicone gum content, such as for example 25 to 50 percent by weight of dimethylsilicone gum, are highly effective as components for skin care formulations from a cost and processing consideration as well. These bi-modal silicones having a higher gum content typically have a viscosity exceeding 50,000 centipoise at 25° C.

While the process of this invention is useful for emulsifying a bi-modal silicone having a viscosity of less than 50,000 centipoise, and providing a stable emulsion thereof, the present process has particular utility for emulsifying a bi-modal silicone having a viscosity of greater than 50,000 centipoise.

Another preferred silicone for the process and compositions of this invention is a resinous silicone. By a resinous silicone it is meant herein a liquid or semisolid organopolysiloxane that has the above-noted general formula wherein a has a value of from 1.0 to 1.9, preferably from 1.3 to 1.7, and contains significant amounts, such as up to 25% by weight, of silicon-bonded hydroxy and/or alkoxy, typically methoxy, radicals. Said silicon-bonded hydroxy and/or alkoxy radicals are reactive so that the silicone resin can be converted to a solid form and/or reacted with other components such as silicone fluids and/or liquid organic resins bearing reactive sites.

Silicone resins are well known in the silicone art and need no detailed delineation herein. Briefly, silicone resins are typically prepared by hydrolyzing one or more hydrolyzable organosilanes and, optionally, "bodying" the hydrolyzate to effect the formation of siloxane linkages. The organic groups of the organosilanes can be any of the hydrocarbon or substituted hydrocarbon radicals delineated above; however, they are typically methyl radicals and mixtures thereof with phenyl radicals. For example the methyl and phenyl radicals can be introduced into the silicone resin as various mixtures of dimethylsiloxy units and monophenylsiloxy units. The hydrolyzable radicals of the organsilanes are typically chlorine or methoxy radicals, although other hydrolyzable radicals are sometimes used.

A preferred silicone resin in this invention, not made by the typical hydrolysis method, consists essentially of the reaction product of a polymethylhydrogensiloxane and a trimethylsilylated silica resin. This reaction product is made according to the process of Blizzard and Swihart, U.S. Pat. No. 4,310,678, which is incorporated herein to show its preparation. Briefly, this reaction product can be prepared by forming a homogeneous mixture having an acid number greater than zero and comprising an organic solvent solution of from 40 to 60 parts by weight of a resinous copolymeric siloxane containing silicon-bonded hydroxyl radicals and 40 to 60 parts by weight of a methylhydrogenpolysiloxane and heating the homogeneous mixture to remove substantially all of the organic solvent therefrom. The resinous copolymeric siloxane contains silicon-bonded hydroxyl radicals and consists essentially of $(CH_3)_3SiO_{\frac{1}{2}}$ siloxane units and $SiO_{4/2}$ siloxane units wherein the ratio of the former to the latter, on a molar basis, has a value of from 0.6/1 to 0.9/1. The methylhydrogenpolysiloxane contains an average of at least one silicon-bonded hydrogen atom per molecule.

The process and compositions of this invention incorporate nonionic primary, secondary and tertiary surfactants to aid in the forming, stabilizing and thickening of the oil-in-water emulsions of this invention.

Nonionic surfactants are well known and need no detailed explanation herein. Nonionic surfactants suitable for use herein are principally of the ethoxylated substrate type wherein the substrate is selected from hydrophobic alcohols, acids, amides, esters and polyoxypropylenes. Suitable surfactants have ES, ESE and SES molecular structures wherein E denotes a polyoxyethylene moiety and S denotes a hydrophobic substrate. The primary, secondary and tertiary surfactants that are used in this invention can be of the same or different type, provided they are nonionic.

The primary surfactant that is used in this invention can be any nonionic surfactant having an HLB number of from 13 to 15; however, it is preferably an ethoxylated alkylphenol such as, for example, octylphenoxypolyethylene oxide containing an average of about 13 ethylene oxide units per molecule and having the CTFA name of octoxynol-13.

The reader is referred to "CTFA Cosmetic Ingredient Dictionary", Third Ed., 1982; the Cosmetic, Toiletry and Fragrance Association, Inc.; Washington, D.C. 20005, hereby incorporated by reference to further delineate the octoxynol nomenclature.

The HLB number of a surfactant is a well-known quantity and needs no explanation herein. The reader is referred to "McCutcheon's Detergents and Emulsifier"; Ridgewood, NJ; Allured Publishing Corp., incorporated herein by reference, for a comprehensive tabulation of surfactants in terms of HLB number, molecular structure, generic name and trade name.

The secondary surfactant that is used in this invention can be any nonionic surfactant having an HLB number of from 7 to 9; however it is preferably an ethoxylated alkylphenol such as, for example, octylphenoxypolyethylene oxide containing an average of about 3 ethylene oxide units per molecule and having the CTFA name of octoxynol-3.

The tertiary surfactant that is used in this invention can be any nonionic surfactant having an HLB number of at least 16; however, it is preferably an ethoxylated saccharide such as, for example, polyethoxylated methyl glucose dioleate containing about 120 ethylene oxide units per molecule and having the CTFA name of PEG-120 methyl glucose dioleate.

The amounts of the primary and secondary surfactants that are used in this invention are related to each other and to the amount of water-insoluble oil that is used.

Thus, for every 100 parts by weight of water-insoluble oil at least 3 millimols of primary surfactant is used. Preferably the amount of primary surfactant that is used in this invention will be from 5 to 50 millimols and most preferably from 10 to 25 millimols per 100 parts by weight of water-insoluble oil.

Herein the term millimols is to be taken in the same sense as the term parts by weight is taken. Thus, if the term parts by weight is applied on a gram basis, for example, the term millimol is to be applied on a milligram-mol basis.

The amount of secondary surfactant to be used in this invention is from 1 to 5, preferably 2 to 3, millimols for every millimol of primary surfactant that is used.

In terms of a preferred primary surfactant, i.e., $C_8H_{17}C_6H_4(OCH_2CH_2)_nOH$ wherein n has an average value of 13, and a preferred secondary surfactant, i.e., $C_8H_{17}C_6H_4(OCH_2CH_2)_nOH$ wherein n has an average value of 3, the amounts of each to use in this invention are at least 2.3, preferably 3 to 30 and most preferably 7.8 to 19.5, parts by weight of the former and at least 2.2, preferably 3.5 to 35 and most preferably from 11 to 19, parts by weight of the latter.

The amount of the tertiary surfactant that is to be used in this invention is surprisingly small, ranging up from about 0.05 millimol per 100 parts by weight of water-insoluble oil. While the actual upper and lower limits of the amount of tertiary surfactant have not been fully delineated the practical limits thereof appear to be from about 0.05 to about 0.25 millimol per 100 parts by weight of water-insoluble oil.

In terms of a preferred tertiary surfactant, i.e., PEG-120 methyl glucose dioleate, the amount to be used in this invention ranges from about 0.3 part by weight, preferably from 0.3 to 1.5 parts by weight for every 100 parts by weight of the water-insoluble oil.

In the process and compositions of this invention the amount of water to be used, is not narrowly limited provided an emulsion can be formed with the amount used. For example, from 10 to 2,000 parts by weight of water for every 100 parts by weight of water-insoluble oil can be used. However, emulsions which are rich in water require longer periods of mixing than emulsions which are rich in water-insoluble oil. Consequently the amount of water to be used in this invention to form the emulsion is preferably limited to less than 350 parts by weight, and most preferably less than 100 parts by weight, per 100 parts by weight of water-insoluble oil. The water that is used in this invention should be clear and clean and has been preferably deionized or distilled.

In those instances wherein the oil phase has a viscosity of greater than 50,000 centipoise at 25° C., such as for example an oil phase consisting essentially of a bi-modal silicone containing from 25 to 50 percent by weight of a silicone gum, it is preferred to limit the amount of water to from about 15 to 45 parts by weight, based on 100 parts by weight of water-insoluble oil.

The compositions of this invention can be diluted with water, if desired. For example, an emulsion composition of this invention containing 15 parts by weight water can be prepared and then diluted with water to an emulsion composition of this invention containing as much as 95 percent water.

The process and composition of this invention can further incorporate nonessential components such as thickeners, biostats, freeze-thaw stabilizers, colorants and odorants which are commonly used in silicone-in-water emulsions and, particularly, in emulsions for personal care compositions.

The compositions of this invention are prepared by the process of this invention which generally comprises mixing suitable amounts of the above-described water-insoluble oil, the primary, secondary and tertiary surfactants and the water and thereafter further processing the mixture to form an emulsion having an average oil particle size of less than about 2 micrometers.

It should be noted that the emulsions of this invention that are prepared from a bi-modal silicone will have emulsion particles of widely varying sizes.

The emulsions of this invention are preferably prepared by mixing an aqueous phase comprising the water and the nonionic tertiary surfactant with an oil phase comprising the water-insoluble oil and the nonionic primary and secondary surfactants.

While it is possible to mix the aqueous phase with the oil phase in any manner it is highly preferred to slowly admix the aqueous phase into the oil phase so that the mixture progresses from an oil-out to a water-out mixture.

The mixing is conducted until the mixture becomes a water-out emulsion and the desired size of oil particle is obtained.

Any mixing means can be used in the process of this invention provided only that it is capable of intimately mixing the components of the emulsion to be prepared. Examples of suitable mixing means include, but are not limited to, impeller mixers, sigma blade dough mixers and planetary mixers.

The compositions prepared by the method of this invention are expected to have the same utility as other oil-in-water emulsions of the art such as for lubricating or coating. The bi-modal emulsion compositions of this invention have particular utility in the formulations of personal care composition such as skin care, antiperspirant, deodorant and hygiene compositions.

The following examples are disclosed to further teach how to practice, and not to limit, the present invention which is properly delineated by the appended claims.

Viscosities were measured at 25° C. in units of centipoise and were converted to pascal-seconds (Pa.s) for this disclosure by multiplying by 0.001. All parts and percentages are by weight. Plasticity numbers were measured according to ASTM D926-67 which is incorporated herein by reference.

Centrifuge stability was determined by spinning the emulsion at 3,000 revolutions per minute for 30 minutes, using a typical laboratory centrifuge. The sample was then visually examined for the presence of separation, settling and oiling. Results are qualitatively stated as none, slight or considerable with respect to each observation.

Freeze-thaw stability was determined by freezing the sample at −15° C. for at least 4 hours and then melting the sample. The observations noted above were made after each freeze-thaw cycle.

EXAMPLE 1

An oil phase was prepared by mixing a bi-modal polydimethylsiloxane fluid, 100 parts, having a viscosity of about 4 Pa·s and consisting of about 87 percent of a mixture of volatile cyclopolydimethylsiloxanes and about 13 percent of a nonvolatile polydimethylsiloxane having a plasticity number of about 150, 5.03 parts of octylphenoxypolyethylene oxide having the CTFA name octoxynol-13 and 4.85 parts of octylphenoxypolyethylene oxide having the CTFA name octoxynol-3 until homogeneous.

An aqueous phase was prepared by mixing 68.3 parts of water, 1.4 parts of PEG-120 methyl glucose dioleate (hereinafter PEG-120 MGD) and 2.5 parts of propylene glycol.

The aqueous phase was added to the oil phase using an air-driven stirrer at high speed. The resulting oil-in-water emulsion had a viscosity of 14.6 Pa.s, a particle size of less than 1 micrometer, as seen in an optical microscope, centrifuge stability and only slight oil separation after 5 freeze-thaw cycles. The siloxane content of this emulsion was about 60% based on siloxane plus water.

For comparison, when this preparation was repeated using Methocel ® (The Dow Chemical Company; Midland, Mich.) as a thickening agent instead of PEG-120

MGD an emulsion was obtained which had a large particle size distribution, a viscosity of 7.7 Pa·s and no freeze-thaw stability.

For further comparison this example was repeated except the PEG-120 MGD was replaced with an equal quantity of PEG-20 methyl glucose sesquistearate, a nonionic emulsifier having a calculated HLB value of 15. Although an emulsion was formed, it contained large-sized emulsion particles and the emulsion separated on standing overnight. In an attempt to get a better emulsion this comparison example was repeated, except the oil phase and the aqueous phases were heated to 75° C. prior to their intermixing. Identical results were obtained.

EXAMPLE 2

The preparation of Example 1 was repeated except the aqueous phase consisted of 16.7 parts of water, 0.3 part of PEG-120 MGD and 2.5 parts of propylene glycol and the mixing was done with a sigma blade dough mixer for 4 hours. The resulting oil-in-water emulsion was a thick gel wherein at least 80% of the particles had a size less than 1 micrometer.

The thick gel was then diluted with 57.6 parts of a 2% solution of PEG-120 MGD in water. The resulting oil-in-water emulsion had a viscosity of 3.9 Pa.s and only slight oil separation after centrifuging or after 5 freeze-thaw cycles. The siloxane content of this emulsion was about 60%, based on siloxane plus water.

EXAMPLE 3

An oil phase was prepared by mixing a bi-modal polydimethylsiloxane fluid, 100 parts, having a viscosity of about 250 Pa·s and consisting of about 70 percent of a mixture of volatile cyclopolydimethylsiloxanes and about 30 percent of a nonvolatile polydimethylsiloxane having a plasticity number of about 150, 11.36 parts of octoxynol-13 and 11.2 parts of octoxynol-3 until homogeneous.

An aqueous phase was prepared by mixing 17.3 parts of water, 0.35 part of PEG-120 MGD and 2.5 parts of propylene glycol as a freeze-thaw stability additive.

The aqueous phase was admixed into the oil phase using a sigma blade dough mixer. The resulting water-in-oil emulsion was then treated with another 15.4 parts of water and 0.3 part of PEG-120 MGD for about 2 hours. The resulting clear gel emulsion was now the desired oil-in-water type and 95% of the particles thereof had a size of 1 micrometer or less.

When this preparation was repeated except that the aqueous phase contained 68.4 parts of water and 1.4 parts of PEG-120 MGD the resulting emulsion had particles which were largely (75%) in the 1 to 2 micrometer range in size, and some were as large as 6 micrometers.

When the above-described preparation was repeated except that the aqueous phase consisted only of 69.8 parts of water and 2.5 parts of propylene glycol, i.e., the PEG-120 MGD was omitted, only 30% of the particles has a size of 2 micrometers or less and 70% of the particles has a size of 3 to 10 micrometers.

This example illustrates the improvement in particle size that can be obtained by the method of this invention comprising the use of a tertiary surfactant and, preferably a limited amount of water.

When the clear gel emulsion noted above was diluted with 57.5 parts of a 2% aqueous solution of PEG-120 MGD an oil-in-water emulsion was obtained which had a viscosity of 26 Pa·s, centrifuge stability and only slight oiling after 5 freeze-thaw cycles.

EXAMPLE 4

A bi-modal polydimethoxysiloxane fluid, 100 parts, having a viscosity of about 2 kPa·s and consisting of an equal weight mixture of the volatile and nonvolatile dimethylsiloxanes disclosed in Example 3 was thoroughly mixed with 19.1 parts of octoxynol-13 and 18.4 parts of octoxynol-3, using a sigma blade dough mixer until homogeneous. An aqueous phase containing 15.5 parts of water, 0.3 part of PEG-120 MGD and 2.5 parts of propylene glycol was slowly added to the homogeneous oil-containing phase with mixing for 100 minutes. The resulting thick, white gel was an oil-in-water emulsion having particles of 1 micrometer or less in size. This gel was diluted with 56.7 parts of distilled water, using the same mixer, to provide an oil-in-water emulsion having a siloxane content of 55%, based on siloxane plus water, and a viscosity of 240 Pa·s.

EXAMPLE 5

The preparation described in Example 4 was repeated except the aqueous phase consisted of 32.6 parts of water, 0.66 part of PEG-120 MGD and 2.5 parts of propylene glycol and the emulsion was mixed for 180 minutes instead of 100 minutes. The resulting oil-in-water emulsion was then diluted with 89.1 parts of water, using the same mixer, to provide an oil-in-water emulsion having a viscosity of 66 Pa.s and a siloxane content of 45%, based on siloxane plus water. Further dilution with water to 35% siloxane content reduced the viscosity to 1 Pa.s and provided an oil-in-water emulsion having stability to centrifugation and to 5 freeze-thaw cycles.

EXAMPLES 6 to 9

Four oil phases were prepared by thoroughly mixing, for each, 50 parts of the bi-modal polydimethylsiloxane fluid described in Example 1, 19.2 parts of octoxynol-13, 18.6 parts of octoxynol-3 and 50 parts of one of the following oils: (i) an equal weight mixture of white petrolatum and mineral oil, (ii) an equal weight mixture of mineral oil and glycerine, (iii) an equal weight mixture of glycerine and volatile cyclopolydimethylsiloxane and (iv) an equal weight mixture of mineral oil and volatile cyclopolydimethylsiloxanes.

Four aqueous phases were prepared by mixing, for each, 47.6 parts of water, 0.97 part of PEG-120 MGD and 2.6 parts of propylene glycol.

Using an air-driven stirrer at high speed an aqueous phase was mixed into each of the four oil phases to provide, in the cases of (i) and (ii), a thick fluid emulsion and, in the cases of (iii) and (iv), a clear gel emulsion.

Each of the four emulsions was further diluted with 49.3 parts of water to provide emulsion compositions of this invention.

EXAMPLE 10

A bi-modal polydimethylsiloxane fluid, 100 parts, having a viscosity of 44 Pa·s and consisting of 20 parts of the nonvolatile dimethylsiloxane and 80 parts of the volatile dimethylsiloxane described in Example 3 was thoroughly mixed with 7.6 parts of octoxynol-13 and 7.4 parts of octoxynol-3 using an air-driven stirrer at high speed to provide an oil phase.

An aqueous phase was prepared by mixing 68.3 parts of water, 1.4 parts of PEG-120 MGD and 2.5 parts of propylene glycol.

The aqueous phase was admixed with the oil phase, using the air stirrer, for 20 minutes to provide an oil-in-water emulsion having a viscosity of 18.5 Pa.s, centrifuge stability, freeze-thaw stability and a dual distribution of particles, the large particles being in the 1 to 3 micrometer size range.

EXAMPLE 11

This example illustrates the preparation, without the use of additional heat, of a petrolatum-in-water emulsion.

An oil phase was prepared by mixing 100 parts of white petrolatum with 19.2 parts of octoxynol-13 and 18.6 parts of octoxynol-3.

An aqueous phase was prepared by mixing 33.7 parts of a 2% aqueous solution of PEG-120 MGD and 2.6 parts of propylene glycol.

The aqueous phase was thoroughly mixed into the oil phase to provide a white gel-like emulsion of the oil-in-water type. This emulsion was further diluted with 116.6 parts of the 2% aqueous solution of PEG-120 MGD.

EXAMPLE 12

An oil phase was prepared by mixing 50 parts of white petrolatum, 50 parts of the bi-modal polydimethylsiloxane fluid described in Example 1, 19.2 parts of octoxynol-13 and 18.6 parts of octoxynol-3. An aqueous phase was prepared by mixing 38.7 parts of a 2% aqueous solution of PEG-120 MGD and 2.6 parts of propylene glycol. The aqueous phase was slowly and thoroughly admixed into the oil phase to provide a thick white gel, which was then diluted with 101.7 parts of water to provide an oil-in-water emulsion of this invention.

EXAMPLE 13

This example illustrates the process of this invention applied to a two-part curable silicone composition. Part I of the curable composition consisted of 65.3% a vinyl functional polydimethylsiloxane fluid, 31.2% of a siliconized high surface area silica filler, 3.5% of a methylhydrogensiloxane crosslinking agent and a trace of a platinum catalyst inhibitor. Part II of the curable composition consisted of 68.3% of the vinyl functional polydimethylsiloxane fluid, 31.5% of the treated silica filler and 0.2% of a platinum-containing catalyst.

Parts I and II, 100 parts of each, were each mixed with 9.5 parts of octoxynol-13 and 9.2 parts of octoxynol-3 to provide two oil phases. Two aqueous phases were prepared by mixing 100 parts of water, 10.2 parts of PEG-120 MGD and 2.5 parts of propylene glycol. Each oil phase was stirred with an air-driven stirrer and the aqueous phase admxed therein. In each case a stable emulsion having particles of 0.5 micrometer or less was obtained.

Equal portions of each emulsion, 75 parts of each, were blended and the blend was diluted with 40 parts of distilled water to give a stable emulsion which did not appear to experience any curing at room temperature for 16 hours. However, when the diluted blend was poured into a mold and heated at 150° C. it cured to a elastomeric material.

EXAMPLE 14

This example illustrates the process of this invention applied to a silicone fluid bearing amino-substituted hydrocarbon radicals. An oil phase was prepared by mixing 100 parts of a trimethylsiloxy-terminated linear organopolysiloxane fluid containing about two siloxane units bearing an aminoethylamino-substituted butyl radical and about 98 siloxane units bearing methyl radicals, 5.6 parts of octoxynol-13 and 5.6 parts of octoxynol-3. An aqueous phase was prepared by mixing 55.8 parts of a 2% aqueous solution of PEG-120 MGD and 2.5 parts of propylene glycol. The oil phase was slowly and thoroughly admixed into the aqueous phase to provide an oil-in-water emulsion wherein the oil particles had sizes of 1 micrometer or less.

EXAMPLE 15

This example illustrates the process of this invention applied to a silicone fluid bearing carboxy-substituted hydrocarbon radicals. An oil phase was prepared by mixing 100 parts of a trimethylsiloxy-terminated linear organopolysiloxane fluid containing about two siloxane units bearing a $-CH_2CH_2SCH_2COOH$ radical and about 98 siloxane units bearing methyl radicals, 6.5 parts of octoxynol-13 and 6.5 parts of octoxynol-3. An aqueous phase was prepared by mixing 55.8 parts of a 2% aqueous solution of PEG-120 MGD and 2.5 parts of propylene glycol. The oil phase was slowly and thoroughly admixed into the aqueous phase to provide an oil-in-water emulsion wherein the oil particles had sizes of 0.1 micrometer or less.

EXAMPLE 16

This example illustrates the process of this invention applied to a waxy substance. An oil phase was prepared by mixing 100 parts of a synthetic beeswax, 8.8 parts of octoxynol-13 and 8.8 parts of octoxynol-3. An aqueous phase was prepared by mixing 55.8 parts of a 2% aqueous solution of PEG-120 MGD and 2.5 parts of propylene glycol. Both phases were heated to 70° C. and the aqueous phase was slowly and thoroughly admixed into the oil phase to provide an oil-in-water emulsion wherein the oil particles had sizes of 1 micrometer or less.

EXAMPLE 17

This example illustrates the process of this invention applied to a solvent solution of a dimethylsilicone gum. An oil phase was prepared by mixing 100 parts of a toluene (20%) solution of a hydroxy-terminated polydimethylsiloxane having a degree of polymerization of about 10,000 (80%), 7.5 parts of octoxynol-13 and 6.3 parts of octoxynol-3. An aqueous phase was prepared by mixing 66.7 parts of a 2% aqueous solution of PEG-120 MGD and 3.5 parts of propylene glycol. The aqueous phase was slowly admixed into the oil phase to provide a thick oil-in-water emulsion wherein the oil particles had sizes of 1 to 1.5 micrometers.

EXAMPLE 18

This example illustrates the process of this invention applied to an hydrolyzate of a diorganodichlorosilane. An oil phase was prepared by mixing 120 parts of a hydrolyzate of phenylmethyldichlorosilane having a hydroxyl content of about 4.5%, 8.5 parts of octoxynol-13 and 8.3 parts of octoxynol-3. An aqueous phase was prepared by mixing 76.2 parts of water, 5.1 parts of PEG-120 MGD and 3.0 parts of propylene glycol. A portion, 31.2 parts, of the aqueous phase was slowly admixed into the oil phase to provide a thick emulsion which was allowed to stir for about 5 minutes. Then the balance of the aqueous phase was slowly added to give an oil-in-water emulsion wherein the oil particles had sizes of less than 0.5 micrometer.

EXAMPLE 19

This example illustrates the process of this invention applied to a volatile silicone. An oil phase was prepared by mixing 100 parts of polydimethylcyclotetrasiloxane, 2.3 parts of octoxynol-13 and 2.3 parts of octoxynol-3. An aqueous phase was prepared by mixing 25 parts of water, 2.2 parts of PEG-120 MGD and 2.5 parts of propylene glycol. The oil phase was slowly admixed into the aqueous phase using an air-driven propeller stirrer to provide an oil-in-water emulsion, which was then diluted with 42 parts of water to provide an emulsion wherein the oil particles had sizes of 0.5 micrometer or less.

EXAMPLE 20

This example illustrates the process of this invention applied to a fluorosilicone fluid. An oil phase was prepared by mixing 100 parts of a trimethyl-terminated poly(methyl-3,3,3-trifluoropropyl)siloxane having a viscosity of 10 pascal-seconds, 6.0 parts of octoxynol-13 and 6.0 parts of octoxynol-3. An aqueous phase was prepared by mixing 27.6 parts of water and 3.6 parts of PEG-120 MGD. The aqueous phase was slowly admixed into the oil phase using an air-driven propeller stirrer to provide an oil-in-water emulsion, which was then diluted with 56.8 parts of water to provide an emulsion wherein the oil particles had sizes of 0.5 micrometer or less.

EXAMPLE 21

This example illustrates the process of this invention applied to a resinous methylsilicone. An oil phase was prepared by mixing 100 parts of a liquid silicone resin which was the reaction product of equal amounts of trimethylsiloxy-terminated poly(methylhydrogen)siloxane and trimethylsiloxy-terminated silica resin and was prepared by the method of U.S. Pat. No. 4,310,678, 9.0 parts of octoxynol-13 and 9.0 parts of octoxynol-3. An aqueous phase was prepared by mixing 98 parts of water, 2.0 parts of PEG-120 MGD and 4.85 parts of isopropyl alcohol. The aqueous phase was slowly mixed into the oil phase using an air-driven propeller stirrer to provide an oil-in-water emulsion. This emulsion was useful as a modifier for aqueous urethane or poly(vinyl alcohol) solutions.

EXAMPLE 22

This example illustrates the process of this invention applied to a resinous phenylmethylsilicone. An oil phase was prepared by mixing 100 parts of a liquid silicone resin which consisted of 33 mol % dimethylsiloxy units, 67 mol % of monophenylsiloxy units and 16% silicon-bonded methoxy radicals, 6.% parts of octoxynol-13 and 6.5 parts of octoxynol-3. An aqueous phase was prepared by mixing 66.7 parts of a 2% aqueous solution of PEG-120 MGD and 2.5 parts of propylene glycol. The oil phase was slowly mixed into the aqueousphase using an air-driven propeller stirrer to provide an oil-in-water emulsion. When the reverse addition was attempted an emulsion was not formed.

EXAMPLE 23

This example illustrates the process of this invention applied to a resinous methylphenylsilicone. An oil phase was prepared by mixing 100 parts of a liquid silicone resin which consisted of 67 mol % dimethylsiloxy units, 33 mol % of monophenylsiloxy units and 16% silicon-bonded methoxy radicals, 6.5 parts of octoxynol-13 and 6.5 parts of octoxynol-3. An aqueous phase was prepared by mixing 10 parts of a 20% aqueous solution of PEG-120 MGD and 9.6 parts of water. The aqueous phase was slowly mixed into the oil phase using an air-driven propeller stirrer to provide an oil-in-water emulsion which was further diluted with 58 parts of water. This emulsion was useful as a modifier for aqueous urethane or poly(vinyl alcohol) solutions.

EXAMPLE 24

This example illustrates the process of this invention applied to a 100% liquid bis-phenol A/epichlorohydrin resin. An oil phase was prepared by mixing 100 parts of the resin (Epon 828), 9.5 parts of octoxynol-13 and 9.5 parts of octoxynol-3. An aqueous phase was prepared by mixing 51 parts of a 20% aqueous solution of PEG-120 MGD. The aqueous phase was slowly mixed into the oil phase using an air-driven propeller stirrer to provide an oil-in-water emulsion which did not separate after standing overnight.

EXAMPLE 25

This example illustrates the process of this invention applied to a polyfunctional aliphatic isocyanate urethane resin. An oil phase was prepared by mixing 100 parts of the resin (Desmodur N100), 9.5 parts of octoxynol-13 and 9.5 parts of octoxynol-3. An aqueous phase was prepared by mixing 51 parts of a 20% aqueous solution of PEG-120 MGD. The aqueous phase was slowly mixed into the oil phase using an air-driven propeller stirrer to provide an oil-in-water emulsion which did not separate after standing overnight.

That which is claimed is:

1. An oil-in-water emulsion composition consisting essentially of 100 parts by weight of a water-insoluble oil, at least 0.05 millimol of a nonionic tertiary surfactant having an HLB number of at least 16, at least 3 millimols of a nonionic primary surfactant having an HLB number of from 13 to 15, from 1 to 5 millimols, per millimol of said primary surfactant, of a nonionic secondary surfactant having an HLB number of from 7 to 9, and at least 10 parts by weight of water.

2. An oil-in-water emulsion composition according to claim 1 wherein the nonionic primary surfactant is octylphenoxypolyethylene oxide containing an average of about 13 ethylene oxide units per molecule, the nonionic secondary surfactant is octylphenoxypolyethylene oxide containing an average of about 3 ethylene oxide units per molecule and the nonionic tertiary surfactant is polyethoxylated methyl glucose dioleate containing about 120 ethylene oxide units per molecule.

3. An oil-in-water emulsion composition according to claim 1 wherein the water-insoluble oil comprises an organopolysiloxane having the average formula $R_aSiO_{(4-a)/2}$ wherein R denotes a monovalent hydrocarbon or substituted hydrocarbon radical, the substituents of which are selected from the group consisting of radicals containing one or more atoms selected from the group consisting of nitrogen, oxygen, sulfur and halogen, and a has a value of from 1 to 3, said organopolysiloxane optionally containing silicon-bonded radicals selected from the group consisting of hydrogen, alkoxy and hydroxy radicals.

4. An oil-in-water emulsion according to claim 3 wherein the oil phase contains all of the nonionic primary surfactant and all of the nonionic secondary surfactant and the aqueous phase contains all of the nonionic tertiary surfactant; and the nonionic primary surfactant is octylphenoxypolyethylene oxide containing an average of about 13 ethylene oxide units per molecule, the nonionic secondary surfactant is octylphenoxypolyethylene oxide containing an average of about 3 ethylene oxide units per molecule and the nonionic tertiary surfactant is polyethoxylated methyl glucose dioleate containing about 120 ethylene oxide units per molecule.

5. An oil-in-water emulsion composition according to claim 3 wherein the nonionic primary surfactant is octylphenoxypolyethylene oxide containing an average of about 13 ethylene oxide units per molecule, the nonionic secondary surfactant is octylphenoxypolyethylene oxide containing an average of about 3 ethylene oxide units per molecule and the nonionic tertiary surfactant is polyethoxylated methyl glucose dioleate containing about 120 ethylene oxide units per molecule.

6. An oil-in-water emulsion according to claim 3 wherein the organopolysiloxane comprises silicon-bonded substituted hydrocarbon radicals wherein the substituents are selected from the group consisting of amino, amido, carboxy, halogen, mercapto and epoxy.

7. An oil-in-water emulsion composition according to claim 3 wherein the organopolysiloxane comprises a polydimethylsiloxane fluid having a viscosity of at least 30 pascal-seconds at 25° C.

8. An oil-in-water emulsion composition according to claim 7 wherein the polydimethylsiloxane fluid consists essentially of
(i) 10 to 50 percent by weight, based on the weight of the polydimethylsiloxane fluid, of a nonvolatile polydimethylsiloxane portion having a viscosity at 25° C. of at least 10 kilopascal-seconds, and
(ii) 50 to 90 percent by weight, on the same basis, of a volatile polydimethylsiloxane portion selected from cyclopolydimethylsiloxanes having 4 and 5 silicon atoms per molecule.

9. An oil-in-water emulsion composition according to containing from 15 to 45 parts by weight of water and wherein the water-insoluble oil has a viscosity of greater than 50 pascal-seconds at 25° C.

10. An oil-in-water emulsion composition according to claim 9 wherein the nonionic primary surfactant is octylphenoxypolyethylene oxide containing an average of about 13 ethylene oxide units per molecule, the nonionic secondary surfactant is octylphenoxypolyethylene oxide containing an average of about 3 ethylene oxide units per molecule and the nonionic tertiary surfactant is polyethoxylated methyl glucose dioleate containing about 120 ethylene oxide units per molecule.

11. An oil-in-water emulsion composition according to claim 10 further comprising a personal-care component selected from the group consisting of petrolatum, glycerine and mineral oil.

12. An oil-in-water emulsion according to claim 8 wherein the oil phase contains all of the nonionic primary surfactant and all of the nonionic secondary surfactant and the aqueous phase contains all of the nonionic tertiary surfactant.

13. An oil-in-water emulsion according claim 12 wherein the nonionic primary surfactant is octylphenoxypolyethylene oxide containing an average of about 13 ethylene oxide units per molecule, the nonionic secondary surfactant is octylphenoxypolyethylene oxide containing an average of about 3 ethylene oxide units per molecule and the nonionic tertiary surfactant is polyethoxylated methyl glucose dioleate containing about 120 ethylene oxide units per molecule.

14. An oil-in-water emulsion according to claim 13 wherein the polydimethylsiloxane fluid has a viscosity of greater than 50 pascal-seconds at 25° C., the aqueous phase contains from 15 to 45 parts by weight of water, the aqueous phase is admixed into the oil phase and the amount of primary surfactant is at least 10 millimols.

15. An oil-in-water emulsion according to claim 13 wherein the water-insoluble oil further comprises a personal care component selected from the group consisting of petrolatum, mineral oil and glycerine.

16. An oil-in-water emulsion composition according to claim 3 wherein the organopolysiloxane comprises silicon-bonded alkoxy and/or hydroxy radicals, R denotes a monovalent hydrocarbon radical and a has a value of from 1.0 to 1.9.

17. An oil-in-water emulsion composition according to claim 16 wherein the organopolysiloxane comprises a silicon resin consisting essentially of dimethylsiloxy units and monophenylsiloxy units.

18. An oil-in-water emulsion composition according to claim 17 wherein the nonionic primary surfactant is octylphenoxypolyethylene oxide containing an average of about 13 ethylene oxide units per molecule, the nonionic secondary surfactant is octylphenoxypolyethylene oxide containing an average of about 3 ethylene oxide units per molecule and the nonionic tertiary surfactant is polyethoxylated methyl glucose dioleate containing about 120 ethylene oxide units per molecule.

19. An oil-in-water emulsion composition according to claim 16 wherein the organopolysiloxane comprises a silicone resin consisting essentially of the reaction product of a polymethylhydrogensiloxane and a trimethylsilylated silica resin.

20. An oil-in-water emulsion composition according to claim 19 wherein the nonionic primary surfactant is octylphenoxypolyethylene oxide containing an average of about 13 ethylene oxide units per molecule, the nonionic secondary surfactant is octylphenoxypolyethylene oxide containing an average of about 3 ethylene oxide units per molecule and the nonionic tertiary surfactant is polyethoxylated methyl glucose dioleate containing about 120 ethylene oxide units per molecule.

21. An oil-in-water emulsion composition according to claim 16 wherein the nonionic surfactant is octylphenoxypolyethylene oxide containing an average of about 13 ethylene oxide units per molecule, the nonionic secondary surfactant is octylphenoxypolyethylene oxide containing an average of about 3 ethylene oxide units per molecule and the nonionic tertiary surfactant is polyethoxylated methyl glucose dioleate containing about 120 ethylene oxide units per molecule.

22. An oil-in-water emulsion composition according to claim 1 wherein the water-insoluble oil comprises petrolatum.

23. An oil-in-water emulsion composition according to claim 22 wherein the nonionic primary surfactant is octylphenoxypolyethylene oxide containing an average of about 13 ethylene oxide units per molecule, the nonionic secondary surfactant is octylphenoxypolyethylene oxide containing an average of about 3 ethylene oxide units per molecule and the nonionic tertiary surfactant is polyethoxylated methyl glucose dioleate containing about 120 ethylene oxide units per molecule.

* * * * *